(12) United States Patent
Orbay et al.

(10) Patent No.: US 10,058,368 B2
(45) Date of Patent: Aug. 28, 2018

(54) HEADLESS COMPRESSION SCREW (71) Applicant: Skeletal Dynamics, L.L.C., Miami, FL (US)

(72) Inventors: Jorge L. Orbay, Miami, FL (US); Thomas H. Norman, Miami, FL (US); Wilbert L. Duenas, Miami, FL (US)

(73) Assignee: SKELETAL DYNAMICS, LLC, Miami, FL (US)

( * ) Notice: Subject to any disclaimer, the term of this patent is extended or adjusted under 35 U.S.C. 154(b) by 609 days.

(21) Appl. No.: 14/576,300

(22) Filed: Dec. 19, 2014

(65) Prior Publication Data
US 2015/0201984 A1 Jul. 23, 2015

Related U.S. Application Data (60) Provisional application No. 61/920,927, filed on Dec. 26, 2013.

(51) Int. Cl.
*A61B 17/86* (2006.01)
*A61B 17/68* (2006.01)

(52) U.S. Cl.
CPC .......... *A61B 17/863* (2013.01); *A61B 17/864* (2013.01); *A61B 17/8625* (2013.01); *A61B 17/8605* (2013.01); *A61B 2017/681* (2013.01)

(58) Field of Classification Search
CPC ........................................ A61B 17/86–17/869
See application file for complete search history.

(56) References Cited

U.S. PATENT DOCUMENTS

| | | | | |
|---|---|---|---|---|
| 5,536,127 A | * | 7/1996 | Pennig | A61B 17/863 411/397 |
| 5,964,768 A | * | 10/1999 | Huebner | A61B 17/1686 411/115 |
| 6,030,162 A | * | 2/2000 | Huebner | A61B 17/1682 411/263 |
| 6,319,254 B1 | | 11/2001 | Giet et al. | |
| 7,582,107 B2 | * | 9/2009 | Trail | A61B 17/863 606/304 |
| 2004/0210227 A1 | * | 10/2004 | Trail | A61B 17/863 606/916 |
| 2006/0025773 A1 | | 2/2006 | Yevmenenko et al. | |
| 2007/0233122 A1 | * | 10/2007 | Denis | A61B 17/7032 606/247 |
| 2013/0238036 A1 | * | 9/2013 | Sinha | A61B 17/68 606/304 |

* cited by examiner

*Primary Examiner* — Zade Coley
(74) *Attorney, Agent, or Firm* — Lott & Fischer, PL (57) ABSTRACT A bone screw for osteosynthesis is provided with screw threads of different pitch or different lead and various diameters in leading, intermediate and trailing ends. The screw may be used to urge together and compress bones or fragments of bone.

6 Claims, 7 Drawing Sheets

HEADLESS COMPRESSION SCREW

CLAIM OF PRIORITY

This application is being filed as a non-provisional patent application under 35 U.S.C. § 111(b) and 37 CFR § 1.53(c). This application claims priority under 35 U.S.C. § 111(e) to U.S. provisional patent application Ser. No. 61/920,927 filed on Dec. 26, 2013, the contents of which are incorporated herein by reference.

FIELD OF INVENTION

The invention relates generally to bone fasteners and, in particular, headless compression screws used to bring together, and maintain compression, between two or more bones or fragments of a bone to facilitate osteosynthesis.

BACKGROUND OF THE INVENTION

Headless compression screws are known in the art. U.S. Pat. No. 4,175,555 to Herbert discloses a bone screw with leading and trailing end portions, where the pitch of the uniform single thread at the leading end portion is greater than the pitch of the uniform single thread at the trailing end portion and the end portions are separated by a central unthreaded portion axially longer than either end portion. When the thread of the leading end portion torqueably engages a distal bone fragment while the thread of the trailing end portion torqueably engages a proximal bone fragment and the unthreaded portion spans the fracture, the fragments are longitudinally translated together and subsequentially compressed as a result of the differential in pitch between the leading thread and the trailing thread. Because its unthreaded central portion spans the fracture it is inherent to the Herbert screw that longitudinal translation of the distal bone fragment towards the proximal bone fragment is delayed until the threads of the trailing end of the screw begin engaging the proximal bone fragment; compression occurs once the fragments are in contact and the screw is torqued further.

Several patents to Huebner disclose screws with single threads of continuously varying pitch along its length where, generally, the pitch of the thread at the leading end of the screw is greater than the pitch of the thread at the trailing end. As the screw is torqueably engaged into two bones or bone fragments the differential in pitch of the continuously varying thread causes compression of the bone material along the whole length of the threaded portion of the screw, resulting in simultaneous translation and compression of the separated bones or bone fragments.

SUMMARY OF THE INVENTION

It is an object of the instant invention to provide a headless compression screw that will, initially, perform translation of a distal bone or bone fragment towards a proximal bone or bone fragment in order to close the gap between the respective faces of the bones or fractured bone fragments. Once the gap is closed, it is a further object of the instant invention to permit further advance of the screw within the bones or bone fragments while maintaining the gap closure but without significant additional compression between the bones or fragments. A further object of the instant invention is to allow for final controlled compression of the already adjoined bones or fragments to facilitate osteosynthesis.

The present invention achieves these objects by providing a headless compression screw with an elongated shaft including a leading portion, a first intermediate portion, a second intermediate portion and a trailing portion. The leading portion having a single thread defining a first outside diameter and a first pitch, the first intermediate portion being unthreaded, the second intermediate portion having a single thread defining a second outside diameter smaller than the first outside diameter and a second pitch smaller than the first pitch, and the trailing portion having a single thread defining a third outside diameter greater than the first outside diameter and a third pitch equal to, or smaller, than the second pitch.

The present invention similarly achieves these objects by providing a headless compression screw with an elongated shaft including a leading portion, a first intermediate portion, a second intermediate portion and a trailing portion. The leading portion having a double thread defining a first outside diameter and a first lead, the first intermediate portion being unthreaded, the second intermediate portion having a single thread defining a second outside diameter smaller than the first outside diameter and a second lead smaller than the first lead, and the trailing portion having a single thread defining a third outside diameter greater than the first outside diameter and a third lead equal to, or smaller, than the second lead.

In operation, when the headless compression screw of the present invention is torqueably inserted through a first bone fragment and a second bone fragment, the bone fragments are translated longitudinally towards each other. When the bone fragments are adjoining each other, further torqueing of the screw, prior to engagement by the trailing portion of the first bone fragment, will maintain the first bone fragment in contact with the second bone fragment without causing substantial compression to occur between the first bone fragment and the second bone fragment. When further torque is applied to the screw upon engagement by the trailing portion of the first bone fragment, compression will occur between the first bone fragment and the second bone fragment.

DETAILED DESCRIPTION OF THE INVENTION

Throughout this disclosure mention is made of several terms which are defined herein as follows: (a) the term "lead" refers to the measurement of the distance along the screw's longitudinal axis that the screw advances relative to a fixed point upon exercising one complete revolution of the screw about its longitudinal axis; (b) the term "pitch" refers to the distance between adjacent thread crests on a screw; (c) the term "single thread" is used to denote a screw or a screw portion having a single continuous helical thread, with a single thread start, on the screw or screw portion; (d) the term "double thread" is used to denote a screw or a screw portion having two continuous helical threads, with two separate thread starts, on the screw or screw portion.

It should be noted that in the prior art it is common, albeit technically incorrect, to use the terms "lead" and "pitch" interchangeably. This is so because the pitch and lead of a screw having a single thread (which a common configuration) is identical. However the same is not the case for screws having multiple threads, such as double threads. Accordingly, the present disclosure references relative pitches between portions of screws having only single threads. For screws having one or more portions with a multiple thread, lead is referenced. The relationship between pitch and lead is explained in greater detail in FIGS. 6A and 6B below.

Figure 1:
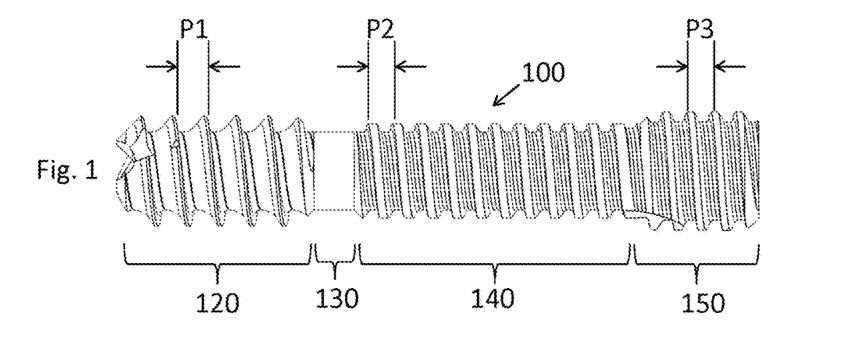
FIG. 1 is a front elevation view of a headless compression screw according to a first embodiment of the present invention in which pitch elements are labeled.

Referring first to FIG. 1, shown is a front elevation view of headless compression screw 100 according to one embodiment of the present invention. Screw 100 includes a leading portion 120 that is threaded with a single thread of pitch P1, a first intermediate portion 130 that is unthreaded, a second clutch portion, as further explained below, 140 that is threaded with a single thread of pitch P2 and a trailing portion 150 that is threaded with a single thread of pitch P3, equal to or smaller than the pitch P2 of the thread of the clutch portion 140. In one embodiment of the instant invention, adapted to join and compress bones or bone fragments, pitch P1 is greater than pitch P2 and pitch P3 is equal to pitch P2. The ratio between pitch P1 and pitch P2 is chosen depending on the particular type of osteosynthesis to be performed. Typical ratios are between 2.0:1.0 and 1.10:1.0 but greater and lesser ratios are also envisioned within the scope of the present invention.

In a further alternate embodiment (not shown) pitch P3 of the thread of the trailing portion 150 is smaller than pitch P2 of the thread of the clutch portion 140. This allows for greater compression between the bones or bone fragments to be joined.

Figure 2:
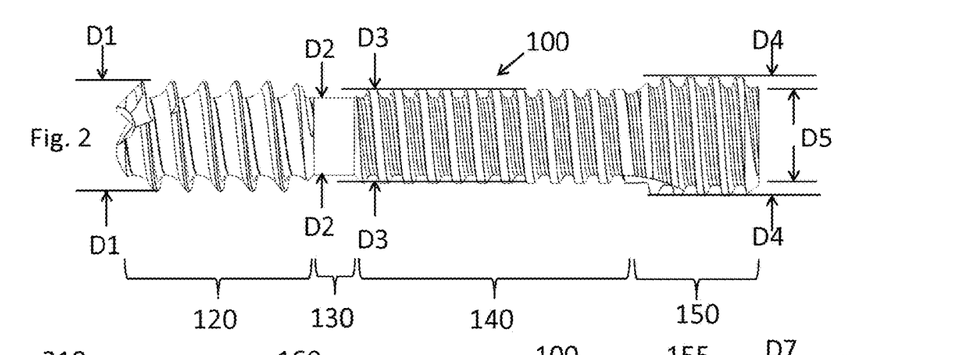
FIG. 2 is a front elevation view of the headless compression screw of FIG. 1 in which diameter elements are labeled.

Referring next to FIG. 2, shown is a front elevation view of screw 100 where the outside diameter of the thread of leading portion 120 is D1 and the outside diameter of the thread of the clutch portion 140 is D3. The first unthreaded intermediate portion 130 has a diameter D2. The root of the thread of the leading portion 120 and the root of the thread of the clutch portion 140 also have a diameter D2. The outside diameter and root diameter of the thread of trailing portion 150 are D4 and D5, respectively. In one embodiment of the present invention diameter D4 is greater than diameter D1, which in turn is greater than diameter D3 (i.e., D4>D1>D3) while diameter D5 is greater than diameter D2 (i.e., D5>D2).

Figure 3:
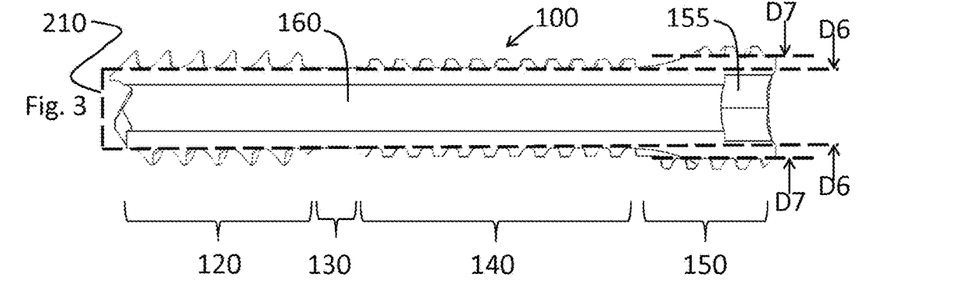
FIG. 3 is a longitudinal cross section of a variation of the headless compression screw of FIG. 1 incorporating a longitudinal cannula.

Referring next to FIG. 3, shown is a longitudinal cross section through one embodiment of screw 100 that includes longitudinal cannula 160 to facilitate placement of the screw over a K-wire and further includes a non-cylindrical driving tool socket 155 at trailing end 150 to permit the application of torque. In one embodiment the threads at leading portion 120 are buttress threads wherein the flatter surface of the thread (the surface closer to being perpendicular to the longitudinal axis of the screw) faces away from the leading portion 120 while the threads at the clutch portion 140 and the trailing portion 150 are reverse buttress, where the flatter surface of the thread faces towards the leading portion 120. The configuration of buttress threads is particularly advantageous when engaging cancellous or spongy bone. However, this feature is not intended to be limiting since other shapes of thread can also be used within the scope of this invention, depending on the type of bone to be joined.

FIG. 3 also shows, in dashed line, a diameter D6 that is substantially identical to diameter D2 of the intermediate unthreaded portion 130. Diameter D6 is the diameter of a pilot hole 210 that can be drilled into the bones or bone fragments to be joined prior to inserting and torqueing screw 100. Also shown in FIG. 3 in dashed line is a diameter D7 that is substantially equal to the diameter D5 of the root of the thread of trailing portion 150. Diameter D7 is the diameter of a pilot hole that can be optionally predrilled in the proximal bone or bone fragment to a depth approximately equal to the length of trailing portion 150.

Referring next to FIGS. 4A-4E, shown, schematically, is the installation of a screw 100 according to one embodiment of the instant invention to achieve the joining and compression of a distal bone or bone fragment 200 and a proximal bone or bone fragment 250 separated by a gap 225. In preparation for joining and compressing the bone fragments, the surgeon drills a pilot hole 210, shown in dashed line, of diameter D6 of a pre-determined length concentrically into distal bone or bone fragment 200 and proximal bone or bone fragment 250. Optionally, the surgeon may also drill into proximal fragment 250 an additional pilot hole (not shown) of diameter D7 of a length approximately equal to the length of screw trailing portion 150. As shown on FIG. 4A the leading portion 120 of the screw 100 is torqueably advanced into proximal fragment 250. This may be done by inserting the cannulated screw 100 over a K-wire (not shown) that stabilizes the position of distal fragment 200 relative to the proximal fragment 250 while allowing longitudinal translation of the fragments.

Figure 4A:
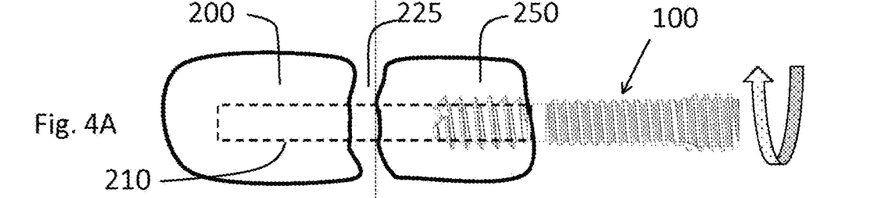
FIGS. 4A-4E show schematically the installation of the headless compression screw of FIG. 1 to achieve the joining and compression of a distal bone or bone fragment and a proximal bone or bone fragment separated by a gap.
Figure 4B:
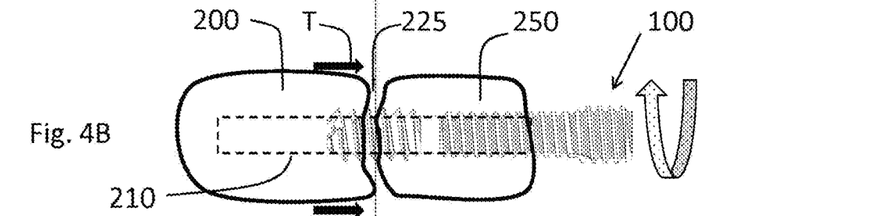

As screw 100 is further torqueably advanced, as shown in FIG. 4B the leading portion 120 of the screw 100 threadably engages the distal fragment 200 while the threaded clutch portion 140 threadably engages the proximal fragment 250. This engagement on both fragments initiates a process of longitudinal translation T (indicated by arrows) of distal fragment 200 towards proximal fragment 250, tending to close gap 225, as the pitch differential between the leading portion 120 and the clutch portion 140 causes the screw 100 to try to advance further into the distal fragment 200 than into the proximal fragment 250. It should be noted that because of the pitch differential, the threads of clutch portion 140 may cross-thread into the helical path previously created in proximal fragment 250 by the thread of leading portion 120. However, clutch portion 140 has a thread that is configured to provide sufficient purchase into proximal bone fragment 250 so that any cross-threading does not impede the translation of distal fragment 200 towards proximal fragment 250, until such time as gap 225 is closed and both fragments are joined at their respective faces at interface line 226.

Figure 4C:
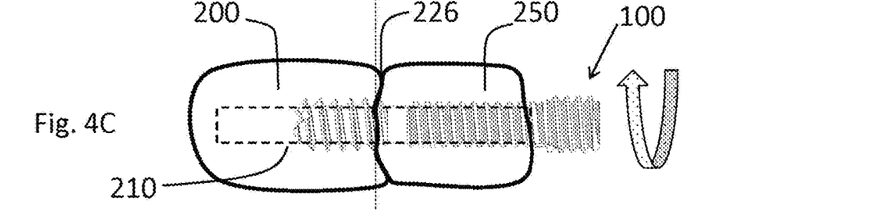
Figure 4D:
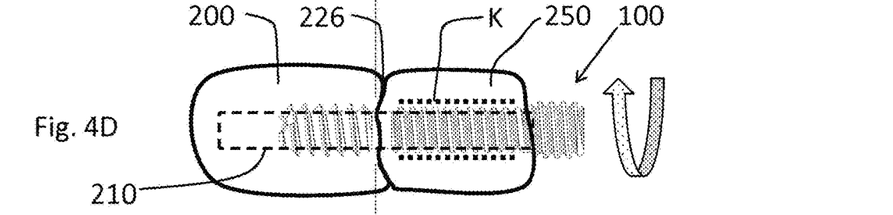

Referring next to FIG. 4C, once gap 225 is closed and both fragments are joined at interface line 226 resistance increases at the now joined bone fragments and any further torqueing of screw 100 into the fragments will cause the thread in the clutch portion 140 to begin a stripping action K of the cancellous bone (an action emulating a slipping clutch) in the region shown by the heavier dotted lines in FIG. 4D, thereby maintaining the contact between the distal fragment 200 and the proximal fragment 250 but without causing significant compression at interface 226.

Figure 4E:
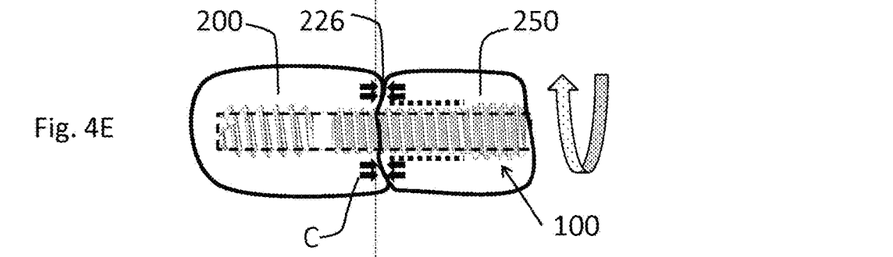

Referring next to FIG. 4E therein is shown the last step in the joining and compressing of the bones or bone fragments. In FIG. 4E it can be seen that trailing portion 150 of screw 100 has been torqueably advanced into proximal fragment 250. Since the outside thread diameter D4 of trailing portion 150 is greater than the thread diameter D1 of leading portion 120, the thread of trailing portion 150 can engage new bone outside of the helical path left by the thread of leading portion 120 in proximal fragment 250 and, therefore, upon further torqueing of screw 100, it has sufficient purchase to again urge the leading portion 120 to move further into the distal fragment 200 than the trailing portion 150 moves into the proximal fragment 250 for every turn of the screw 100. This causes tension in screw 100 that is transmitted by the threads to the bone fragments as compression action C, shown by arrows, at the interface 226 between the distal fragment 200 and the proximal fragment 250. It is be noted that at completion of this step, trailing portion 150 of screw 100 should be preferably fully embedded into proximal fragment 250 in order to avoid impingement with soft tissue.

Figure 5A:
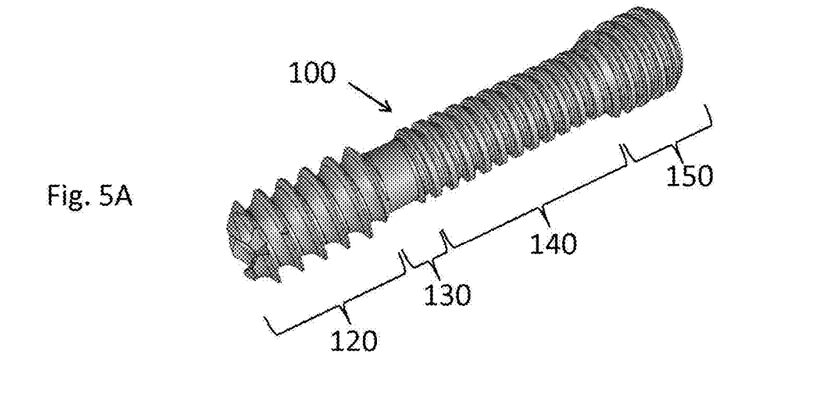
FIGS. 5A-5C are views from different angles of the headless compression screw of FIG. 1 showing the different portions and features thereof.
Figures 5B, 5C:
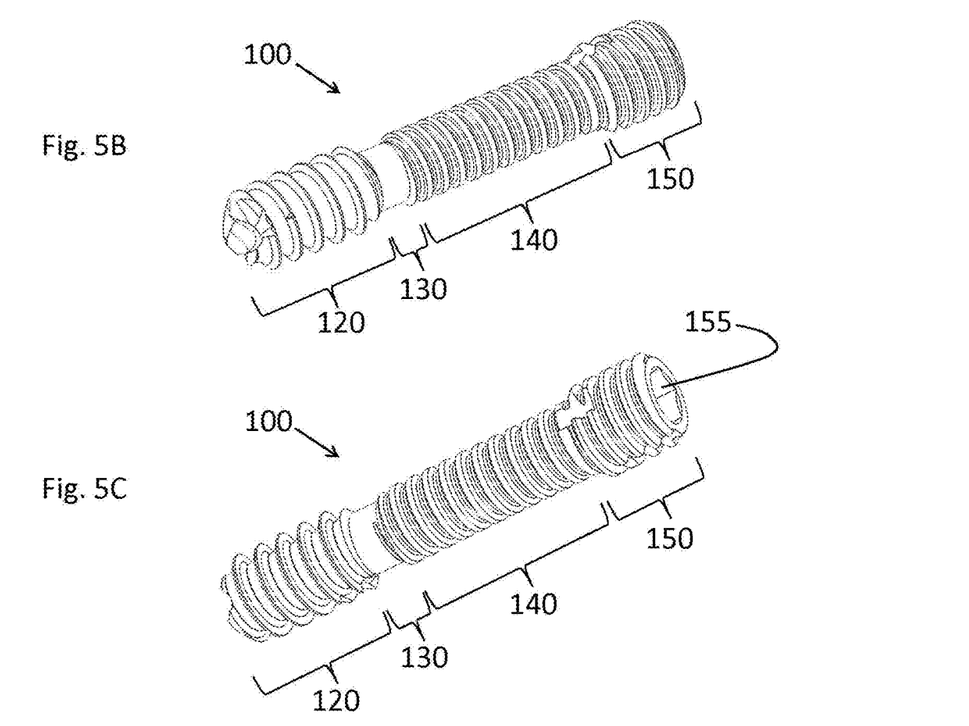

Referring next to FIGS. 5A-5C, shown are views from different angles of headless compression screw 100 indicating the different portions and features thereof according to one embodiment of the present invention.

Figure 6A:
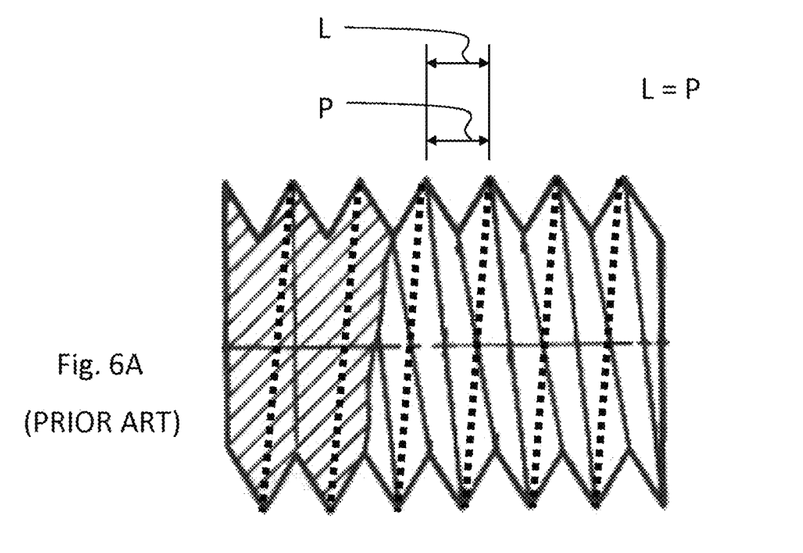
FIG. 6A is a diagrammatic view of a portion of a single threaded screw indicating the relationship between the pitch of the thread and the lead of the thread.
Figure 6B:
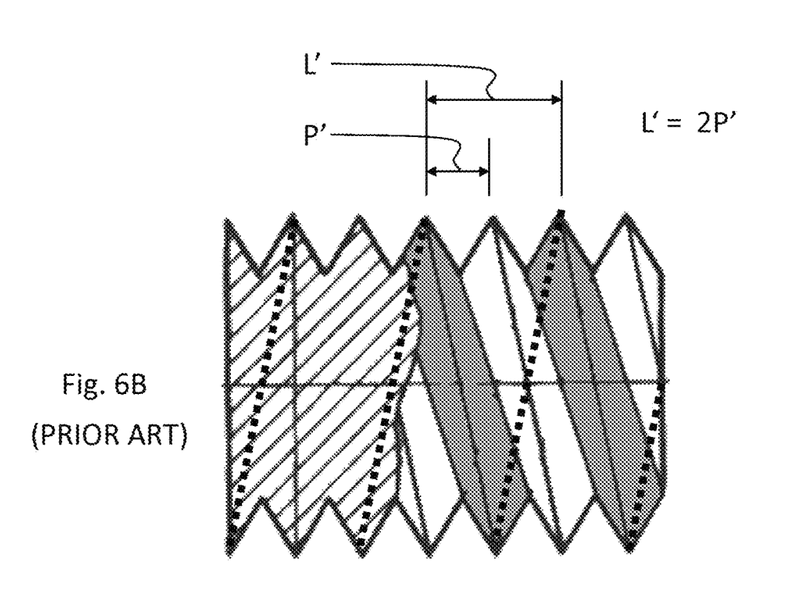
FIG. 6B is a diagrammatic view of a portion of a double threaded screw indicating the relationship between the pitch of the thread and the lead of the thread.

Referring now to FIG. 6A, shown diagrammatically, is a portion of a screw having a single thread, that is, a thread formed by a single helix on a cylinder. In a screw having a single thread the pitch P, that is, the distance measured parallel to the longitudinal axis of the screw between corresponding points on adjacent thread forms is equal to the lead L, that is, the distance, measured parallel to the longitudinal axis of the screw, that the screw moves axially in one complete rotation. FIG. 6B shows diagrammatically a portion of a screw having a double thread, that is, a thread formed by two helices on a cylinder. In a screw having a double thread, the lead L' is equal to twice the pitch P' of the screw. In general, in screws of multiple (i.e.: more than one) thread, the lead of the screw is equal to its pitch multiplied by the number of helices formed in the cylinder.

In the embodiments of the present invention described above, the different threaded portions of the headless compression screw have single threads, albeit of different pitches. It is the difference in pitches between the single threads that achieves the objectives of longitudinal translation and subsequent compression between bones or bone fragments to be joined as the screw is advanced. Below are described embodiments where a double thread is formed in the leading portion of the screw and a single thread is formed in the remaining portions. It is by configuring a differential in leads between the thread of the leading portion and that of the other portions that the objectives of longitudinal translation and subsequent compression between bones or bone fragments to be joined is achieved.

Figure 7:
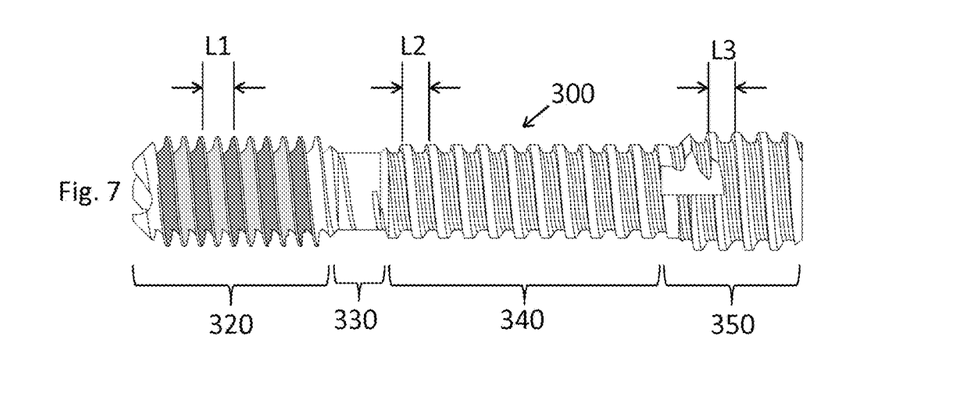
FIG. 7 is a front elevation view of a headless compression screw according to a second embodiment of the present invention in which lead elements are labeled.

Referring now to FIG. 7, shown is a front elevation view of headless compression screw 300 according to one embodiment of the present invention. Screw 300 includes a leading portion 320 that is threaded with a double thread of lead L1, a first intermediate portion 330 that is unthreaded, a second clutch portion, as further explained below, 340 that is threaded with a single thread of lead L2 and a trailing portion 350 that is threaded with a single thread of lead L3, equal to or smaller than the lead L2 of the thread of the clutch portion 340. In one embodiment of the instant invention, adapted to join and compress bones or bone fragments, lead L1 is greater than lead L2 and lead L3 is equal to lead L2. The ratio between lead L1 and lead L2 is chosen depending on the particular type of osteosynthesis to be performed. Typical ratios are between 2.0:1.0 and 1.10:1.0 but greater and lesser ratios are also envisioned within the scope of the present invention.

Figure 8:
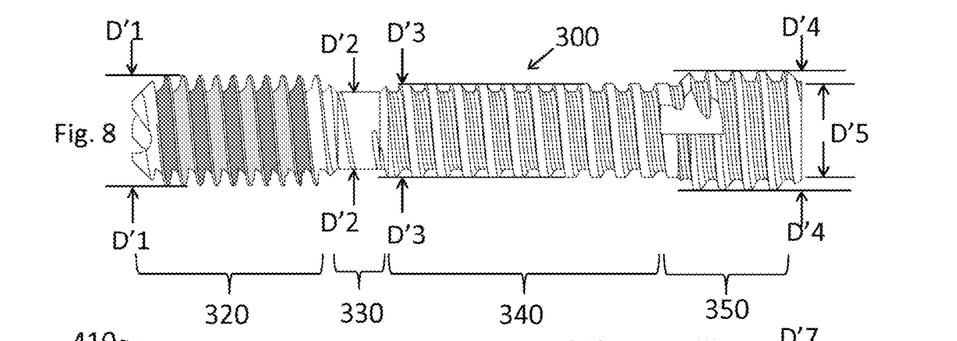
FIG. 8 is a front elevation view of the headless compression screw of FIG. 7 in which diameter elements are labeled.

Referring next to FIG. 8, shown is a front elevation view of screw 300 where the outside diameter of the thread of leading portion 320 is D'1 and the outside diameter of the thread of the clutch portion 340 is D'3. The first unthreaded intermediate portion 330 has a diameter D'2. The root of the thread of the leading portion 320 and the root of the thread of the clutch portion 340 also have a diameter D'2. The outside diameter and root diameter of the thread of trailing portion 350 are D'4 and D'5, respectively. In one embodiment of the present invention diameter D'4 is greater than diameter D'1, which in turn is greater than diameter D'3 (i.e., D'4>D'1>D'3) while diameter D'5 is greater than diameter D'2 (i.e., D'5>D'2).

Figure 9:
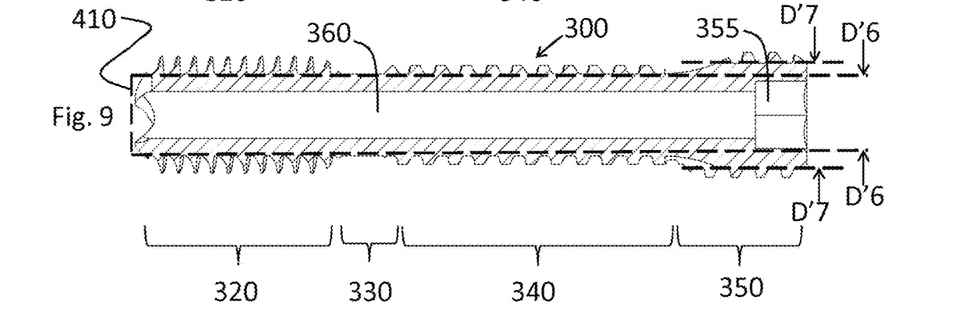
FIG. 9 is a longitudinal cross section of a variation of the headless compression screw of FIG. 7 incorporating a longitudinal cannula.

Referring next to FIG. 9, shown is a longitudinal cross section through one embodiment of screw 300 that includes longitudinal cannula 360 to facilitate placement of the screw over a K-wire and further includes a non-cylindrical driving tool socket 355 at trailing end 350 to permit the application of torque. In one embodiment the threads at leading portion 320 are buttress threads wherein the flatter surface of the thread (the surface closer to being perpendicular to the longitudinal axis of the screw) faces away from the leading portion 320 while the threads at the clutch portion 340 and the trailing portion 350 are reverse buttress, where the flatter surface of the thread faces towards the leading portion 320. The configuration of buttress threads is particularly advantageous when engaging cancellous or spongy bone. However, this feature is not intended to be limiting since other shapes of thread can also be used within the scope of this invention, depending on the type of bone to be joined.

FIG. 9 also shows, in dashed line, a diameter D'6 that is substantially identical to diameter D'2 of the intermediate unthreaded portion 330. Diameter D'6 is the diameter of a pilot hole 410 that can be drilled into the bones or bone fragments to be joined prior to inserting and torqueing screw 300. Also shown in FIG. 9 in dashed line is a diameter D'7 that is substantially equal to the diameter D'5 of the root of the thread of trailing portion 350. Diameter D'7 is the diameter of a pilot hole that can be optionally predrilled in the proximal bone or bone fragment to a depth approximately equal to the length of trailing portion 350.

Referring next to FIGS. 10A-10E, shown schematically, is the installation of a screw 300 according to this embodiment of the present invention to achieve the joining and compression of a distal bone or bone fragment 400 and a proximal bone or bone fragment 450 separated by a gap 425. In preparation for joining and compressing the bone fragments, the surgeon drills a pilot hole 410, shown in dashed line, of diameter D'6 of a pre-determined length concentrically into distal bone or bone fragment 400 and proximal bone or bone fragment 450. Optionally, the surgeon may also drill into proximal fragment 450 an additional pilot hole (not shown) of diameter D'7 of a length approximately equal to the length of screw trailing portion 350. As shown on FIG. 10A the leading portion 320 of the screw 300 is torqueably advanced into proximal fragment 450. This may be done by inserting the cannulated screw 300 over a K-wire (not shown) that stabilizes the position of distal fragment 400 relative to the proximal fragment 450 while allowing longitudinal translation of the fragments.

Figure 10A:
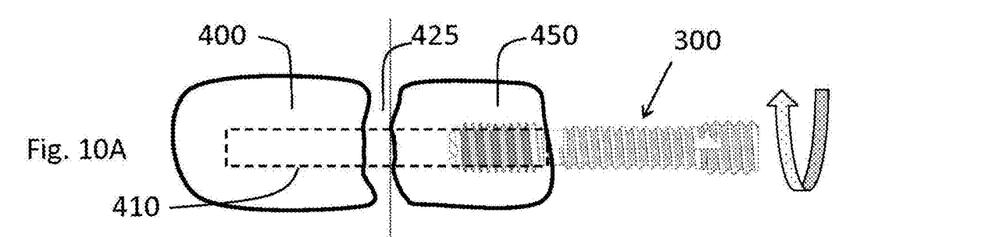
FIGS. 10A-10E show schematically the installation of the headless compression screw of FIG. 7 to achieve the joining and compression of a distal bone or bone fragment and a proximal bone or bone fragment separated by a gap.
Figure 10B:
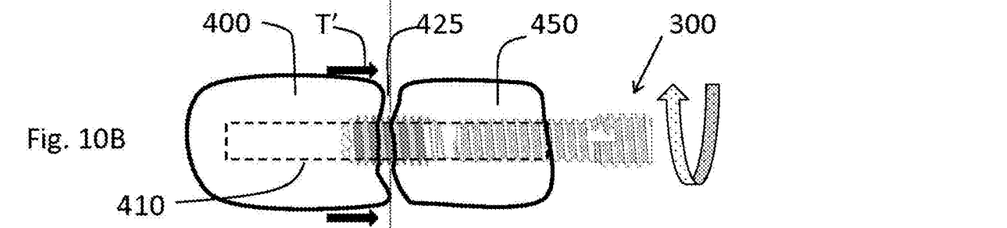

As screw 300 is further torqueably advanced, as shown in FIG. 10B the leading portion 320 of the screw 300 threadably engages the distal fragment 400 while the threaded clutch portion 340 threadably engages the proximal fragment 450. This engagement on both fragments initiates a process of longitudinal translation T' (indicated by arrows) of distal fragment 400 towards proximal fragment 450, tending to close gap 425, as the lead differential between the leading portion 320 and the clutch portion 340 causes the screw 300 to try to advance further into the distal fragment 400 than into the proximal fragment 450. It should be noted that because of the lead differential, the threads of clutch portion 340 may cross-thread into the helical paths previously created in proximal fragment 450 by the double thread of leading portion 320. However, clutch portion 340 has a thread that is configured to provide sufficient purchase into proximal bone fragment 450 so that any cross-threading does not impede the translation of distal fragment 400 towards proximal fragment 450, until such time as gap 425 is closed and both fragments are joined at their respective faces at interface line 426.

Figure 10C:
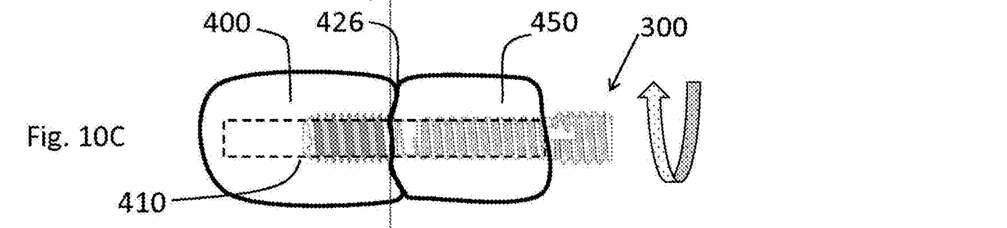
Figure 10D:
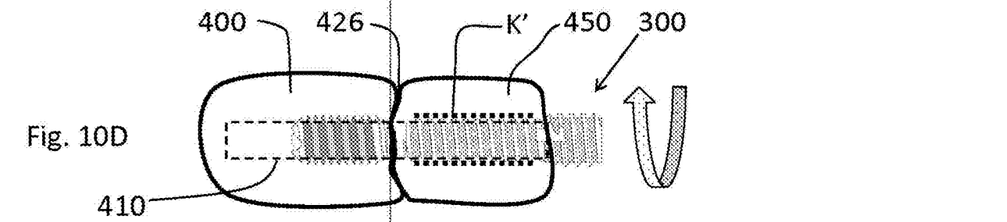

Referring next to FIG. 10C, once gap 425 is closed and both fragments are joined at interface line 426 resistance increases at the now joined bone fragments and any further torqueing of screw 300 into the fragments will cause the thread in the clutch portion 340 to begin a stripping action K' of the cancellous bone (an action emulating a slipping clutch) in the region shown by the heavier dotted lines in FIG. 10D, thereby maintaining the contact between the distal fragment 400 and the proximal fragment 450 but without causing significant compression at interface 426.

Figure 10E:
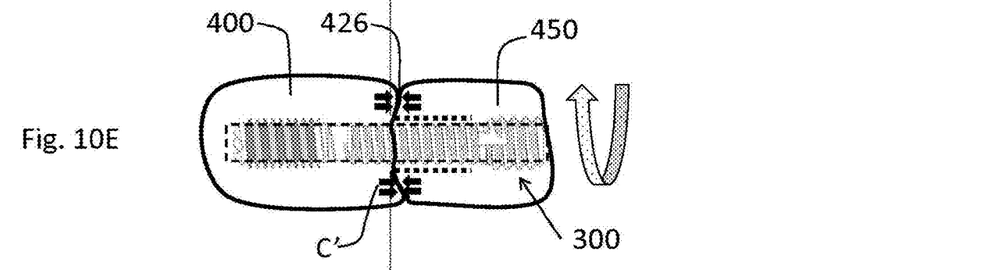

Referring next to FIG. 10E therein is shown the last step in the joining and compressing of the bones or bone fragments. In FIG. 10E it can be seen that trailing portion 350 of screw 300 has been torqueably advanced into proximal fragment 450. Since the outside thread diameter D'4 of trailing portion 350 is greater than the thread diameter D'1 of leading portion 320, the thread of trailing portion 350 can engage new bone outside of the helical paths left by the double thread of leading portion 320 in proximal fragment 450 and therefore, upon further torqueing of screw 300, it has sufficient purchase to again urge the leading portion 320 to move further into the distal fragment 400 than the trailing portion 350 moves into the proximal fragment 450 for every turn of the screw 300. This causes tension in screw 300 that is transmitted by the threads to the bone fragments as compression action C', shown by arrows, at the interface 426 between the distal fragment 400 and the proximal fragment 450. It is to be noted that at completion of this step, trailing portion 350 of screw 300 should be preferably fully embedded into proximal fragment 450 in order to avoid impingement with soft tissue.

Figure 11A:
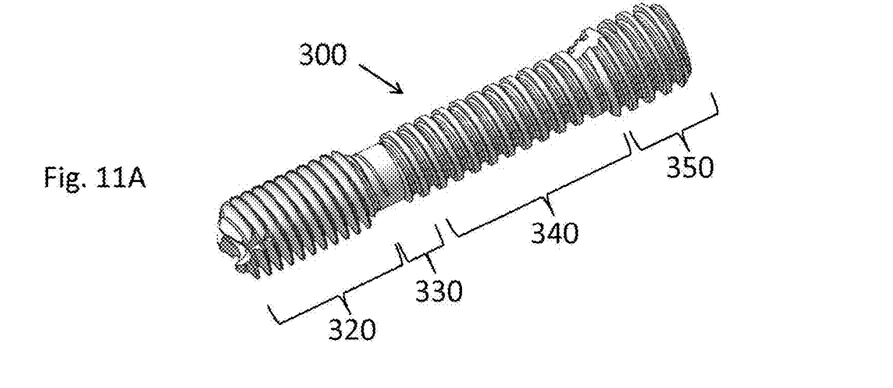
FIGS. 11A-11C are views from different angles of the headless compression screw of FIG. 7 showing the different portions and features thereof.
Figure 11B:
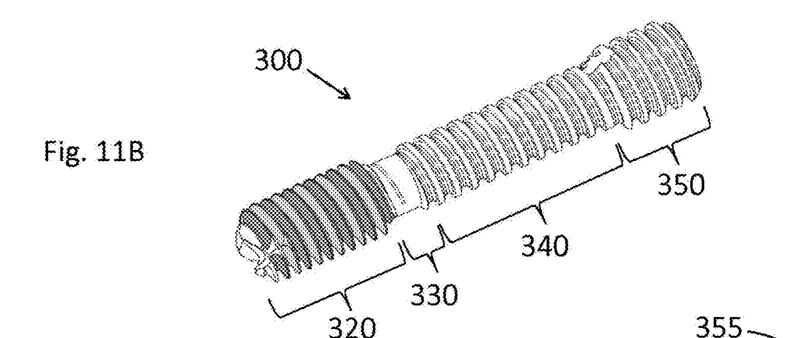
Figure 11C:
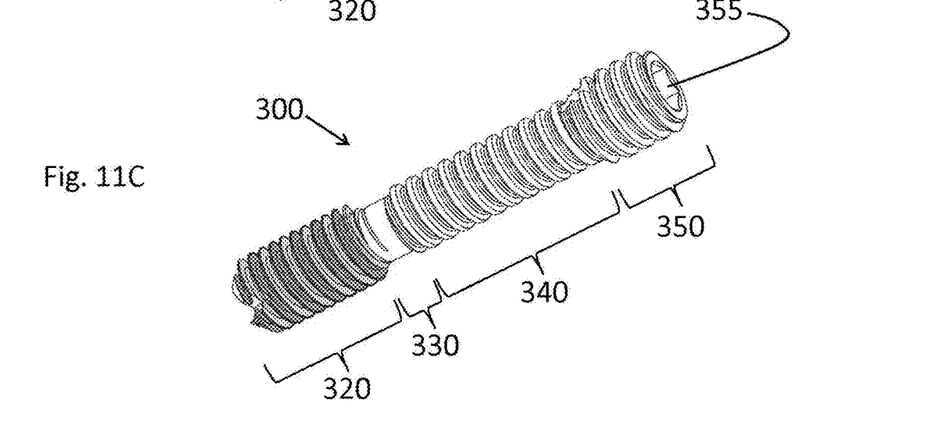

Referring next to FIGS. 11A-11C, shown are views from different angles of headless compression screw 300 indicating the different portions and features thereof according to this further embodiment of the present invention.

Although described above in connection with headless compression screw for osteosynthesis having a particular arrangement of single and double threads, thread shapes, thread diameters, thread pitches and thread leads these descriptions are not intended to be limiting as various modifications may be made therein without departing from the spirit of the invention and within the scope and range of equivalents of the claims. For example, the leading portion of the headless compression screw can be configured with a triple thread while the other portions are configured with a double thread by selecting the appropriate ratio of the dimension of the respective leads in the leading portion versus the other portions. Accordingly, various combinations of thread multiples are possible between the various portions of the disclosed screw to achieve the objects of the present invention without departing from the spirit of the invention.

We claim:

1. A headless compression screw comprising:
an elongated shaft including a leading portion, a first intermediate portion, a second intermediate portion and a trailing portion, said elongated shaft, leading portion, first intermediate portion, second intermediate portion, and trailing portion comprising a single body of unitary construction;
said leading portion having a double thread defining a first outside diameter and a first lead;
said first intermediate portion being unthreaded;
said second intermediate portion having a single thread defining a second outside diameter smaller than said first outside diameter and a second lead smaller than said first lead;
said trailing portion having a single thread defining a third outside diameter greater than said first outside diameter and a third lead smaller than or equal to said second lead;
wherein, when said headless compression screw is torqueably inserted through a first bone or bone fragment and a second bone or bone fragment separated by a gap, said second bone or bone fragment is translated longitudinally towards said first bone or bone fragment;
wherein, when said bone fragments are adjoining each other, further torqueing of said screw, prior to engagement by said trailing portion of said first bone or bone fragment, will maintain said second bone or bone fragment in contact with said first bone or bone fragment without causing substantial compression to occur between said first bone or bone fragment and said second bone or bone fragment, and,
wherein, when further torque is applied to said screw upon engagement by said trailing portion of said first bone or bone fragment, compression will occur between said second bone or bone fragment and said first bone or bone fragment.

2. A screw according to claim 1, wherein the shaft of the screw is cannulated.

3. A screw according to claim 1, wherein the said trailing portion has a non-cylindrical cavity capable of accepting torque from a torqueing tool.

4. A headless compression screw comprising:
an elongated shaft including a leading portion, a first intermediate portion, a second intermediate portion and a trailing portion, said elongated shaft, leading portion, first intermediate portion, second intermediate portion, and trailing portion comprising a single body of unitary construction;
said leading portion having one or more threads defining a first outside diameter and a first lead;
said first intermediate portion being unthreaded;
said second intermediate portion having one or more threads defining a second outside diameter smaller than said first outside diameter and a second lead smaller than said first lead;
said trailing portion having one or more threads defining a third outside diameter greater than said first outside diameter and a third lead smaller than or equal to said second lead;
wherein, when said headless compression screw is torqueably inserted through a first bone or bone fragment and a second bone or bone fragment separated by a gap, said second bone or bone fragment is translated longitudinally towards said first bone or bone fragment;
wherein, when said bone fragments are adjoining each other, further torqueing of said screw, prior to engagement by said trailing portion of said first bone or bone fragment, will maintain said second bone or bone fragment in contact with said first bone or bone fragment without causing substantial compression to occur between said first bone or bone fragment and said second bone or bone fragment, and,
wherein, when further torque is applied to said screw upon engagement by said trailing portion of said first bone or bone fragment, compression will occur between said second bone or bone fragment and said first bone or bone fragment.

5. A screw according to claim 4, wherein the shaft of the screw is cannulated.

6. A screw according to claim 4, wherein the said trailing portion has a non-cylindrical cavity capable of accepting torque from a torqueing tool.

* * * * *